United States Patent [19]

Hansen et al.

[11] Patent Number: 4,847,266
[45] Date of Patent: Jul. 11, 1989

[54] METHOD FOR PREPARING 6-β-HALOPENICILLANIC ACIDS

[75] Inventors: Erik I. Hansen, Fredensborg; Mogens P. Kran-Nielsen, Skovlunde; Welf Von Daehne, Rungsted Kyst, all of Denmark

[73] Assignee: Leo Pharmaceutical Products Ltd., Ballerup, Denmark

[21] Appl. No.: 51,686

[22] PCT Filed: Aug. 18, 1986

[86] PCT No.: PCT/DK86/00090
 § 371 Date: Apr. 28, 1987
 § 102(e) Date: Apr. 28, 1987

[87] PCT Pub. No.: WO87/01371
 PCT Pub. Date: Mar. 12, 1987

[30] Foreign Application Priority Data

Sep. 6, 1985 [GB] United Kingdom ............... 8522156

[51] Int. Cl.⁴ .................. C07D 499/00; A61K 31/43
[52] U.S. Cl. ................................. 514/310; 514/192; 514/195

[58] Field of Search ............... 540/310; 514/192, 193

[56] References Cited

U.S. PATENT DOCUMENTS 4,296,032 10/1981 Dennerly .................. 540/310
4,594,246 6/1986 von Daehne et al. ......... 540/310

Primary Examiner—Nicholas S. Rizzo
Attorney, Agent, or Firm—Cushman, Darby & Cushman

[57] ABSTRACT

The present invention relates to a new and improved method for the preparation of a compound of the formula I

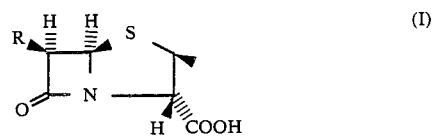

in which R stands for halogen, giving rise to high yields of substantially pure 6β-halopenicillanic acids, obtained in one step.

16 Claims, No Drawings

METHOD FOR PREPARING 6-β-HALOPENICILLANIC ACIDS

The present invention relates to a new and improved method for the preparation of a compound of the formula I

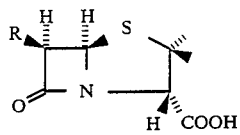

in which R stands for halogen, i.e. chlorine, bromine or iodine, and salts thereof. More particularly, it relates to a new and improved method for the preparation of 6β-halopenicillanic acids and salts thereof, which are known β-lactamase inhibitors enhancing the effectiveness of penicillins and cephalosporins against a wide range of β-lactamase producing bacteria.

It has been reported (J. Org. Chem. Vol. 43 pp. 3611–3613, 1978; Proc. Natl. Acad. Sci. USA. Vol. 75, pp. 4145–4149, 1978; U.S. Pat. No. 4,180,506 (1979); Biochem. J. Vol. 177 pp. 365–367, 1979) that mixtures of 6β- and 6α-bromopenicillanic acid were obtained either by epimerization of the latter or by selective hydrogenation of 6,6-dibromopenicillanic acid. In these references, 6β-bromopenicillanic acid has always been described as the minor component of an inseparable mixture with 6α-bromopenicillanic acid, the former being present in estimated amounts of from 5 to 15%.

It has further been reported (Tetrahedron Letters No. 48, pp. 4631–4634, 1979; U.S. Pat. No. 4,347,182 (1982); U.S. Pat. No. 4,397,783 (1983)) that selective reduction of esters of 6-arylselenyl-6-chloro- or 6,6-dihalopenicillanic acids with tri-n-butyltin hydride or triphenyltin hydride afforded 6β-halopenicillanic acid esters in about 50% yield, together with substantial amounts of the corresponding esters of penicillanic acid and the 6α-halo and 6,6-dihalo derivatives. Following separation of the 6β-halo ester from its contaminants and removal of the ester group by hydrolysis, the free 6β-halopenicillanic acid or a salt thereof containing not more than 5% of the corresponding 6α-epimer was obtained in about 30% yield, based upon the starting 6,6-dihalo ester.

According to British patent application GB No. 2,051,055A and Tetrahedron Letters. Vol. 21 pp. 2991–2994 (1980), similar yields of 6β-halopenicillanic acids or salts thereof were obtained by nucleophilic substitution of 6α-perfluoroalkylsulphonyloxypenicillanic acid esters with halide ions and subsequent hydrolysis of the resulting 6β-halo substituted esters.

The preparation of pure 6β-halopenicillanic acids and base salts thereof from the corresponding 6α-halo derivatives by aqueous equilibration of the latter and subsequent separation of the resulting epimeric mixture has been described in British patent GB No. 2,125,035B and J. Antibiotics Vol. 33 pp. 451–452 (1980). The former reference also discloses the selective reduction of 6,6-dihalopenicillanic acids or salts thereof by treatment with alkali metal borohydrides, tetraalkylammonium boranate or sodium cyanoborohydride to give favourably high yields (>50%) of the free 6β-halopenicillanic acids which were separated from the respective reaction mixtures by column chromatography or by fractionate crystallization.

However, it is a disadvantage of the prior art methods leading to the preparation of 6β-halopenicillanic acids that (i) the introduction and removal of the carboxyl-protecting group requires two additional steps in the overall synthesis, and/or (ii) the separation of the 6β-epimer from undesired by-products requires purification by chromatographic methods or by fractionate crystallization.

It has now surprisingly been found that high yields (up to 70% or more) of substantially pure 6β-halopenicillanic acids can be obtained in one step by the present improved method which comprises base-catalyzed epimerization of a suitable salt of a 6α-halopenicillanic acid suspended in an aqueous-organic solvent mixture with precipitation of the less soluble salt of the corresponding 6β-halopenicillanic acid thus formed. Hereby, the equilibrium of the epimerization reaction, which in solution is strongly in favour of the 6α-epimer, is shifted in the desired direction to provide precipitation of a substantially pure salt of a compound of formula I in a hitherto unseen high yield. This high yield is maintained, even when the process is scaled up, as will appear from the working examples below. The present method is more simple than any of the known processes, gives no separation problems, and is well suited for large scale production.

It is thus an object of the present invention to provide a simple industrial process for the preparation in high yield of substantially pure 6β-halopenicillanic acids and salts thereof without the necessity for additional steps to protect the 3-carboxyl group in the starting materials or to purify the desired reaction products.

The epimerization reaction is generally carried out by suspending a suitable base salt of the 6α-halopenicillanic acid in a suitable solvent mixture consisting of a polar organic solvent and water, and treating said suspension in the presence of a suitable base at a temperature in the range from 20° to 80° C., preferably from 30° to 60° C., for a period of 12 to 180 hours.

Suitable base salts of 6α-halopenicillanic acids for use as starting materials in the process include those formed with selected organic amines, preferably secondary amines, in particular dicyclohexylamine.

Suitable solvents used for suspending the starting material and the reaction product in the process are e.g. mixtures of a polar organic solvent, such as dimethyl sulphoxide, dimethylformamide, dimethylacetamide, diethylformamide, hexamethylphosphoramide or tetrahydrothiophene 1,1-dioxide (sulfolane), and water; the ratio (v/v) between the organic solvent and water varying from 4:1 to 1:4 preferably from 2:1 to 1:2.

Examples of bases used for catalyzing the epimerization process are e.g. sodium and potassium carbonate, trisodium phosphate, and triethylamine, but any inorganic or organic base which is strong enough to speed up the epimerization process without being so strong as to lead to destruction of reagents or reactants, e.g. an opening of the β-lactam ring, can be used.

The precipitated reaction products are recovered in a conventional manner. The compounds of formula I are generally isolated in the form of base salts, favourably as dicyclohexylammonium salts, but can readily be converted into the halopenicillanic acids of formula I by conventional means.

The precipitated 6β-halopenicillanate may, optionally after recrystallization, in a separate step be converted into any other suitable salt, e.g. an alkali metal salt, alkaline earth metal salt, or amine salt including a salt with a β-lactam antibiotic containing a free amino group such as pivampicillin and bacampicillin.

The presence of any 6α-halo compound in the products may be estimated by standard analytical methods including NMR spectroscopy, thin-layer chromatography (TLC) and high performance liquid chromatography (HPLC).

The invention will be further illustrated by the following, non-limiting examples.

mother liquor afforded a 2nd crop of crystalline product which contained the 6α-halo epimer as the major component.

In Table 1 are summarized the results obtained from a series of reactions performed in accordance with the described procedure. The yield of crystalline 6-halopenicillanate recovered in the 1st crop and the α:β ratio of the product are given.

TABLE 1

| Ex. No. | X | Solvent Mixture Ratio | Base | Reaction Temp. (°C.) | Reaction Time (h) | Crystalline material recovered as 1st crop Yield (%) | Crystalline material recovered as 1st crop Ratio α:β | Yield β (%) |
|---|---|---|---|---|---|---|---|---|
| 1a | Cl | DMSO—H$_2$O 1:1 | Na$_2$CO$_3$ | 25 | 72 | 43.9 | 69:31 | 13.6 |
| 1b | Br | DMSO—H$_2$O 1:1 | Na$_2$CO$_3$ | 25 | 72 | 67.3 | 45:55 | 37.0 |
| 1c | I | DMSO—H$_2$O 1:1 | Na$_2$CO$_3$ | 25 | 72 | 62.0 | 32:68 | 42.2 |
| 1d | Br | DMSO—H$_2$O 1:1 | Na$_2$CO$_3$ | 35 | 96 | 66.1 | 5:95 | 62.8 |
| 1e | Br | DMSO—H$_2$O 1:1 | Na$_2$CO$_3$ | 40 | 120 | 67.0 | 1:99 | 66.3 |
| 1f | Cl | DMF—H$_2$O 1:1 | K$_2$CO$_3$ | 25 | 72 | 27.6 | 5:95 | 26.2 |
| 1g | Br | DMF—H$_2$O 1:1 | K$_2$CO$_3$ | 25 | 72 | 57.5 | 5:95 | 54.6 |
| 1h | Cl | DMF—H$_2$O 1:1 | K$_2$CO$_3$ | 25 | 120 | 36.5 | 8:92 | 33.6 |
| 1i | Br | DMF—H$_2$O 1:1 | K$_2$CO$_3$ | 25 | 120 | 46.2 | 5:95 | 43.9 |

DMSO = dimethylsulphoxide,
DMF = dimethylformamide

EXAMPLE 1

Dicyclyhexylammonium 6β- halopenicillanates

Reaction

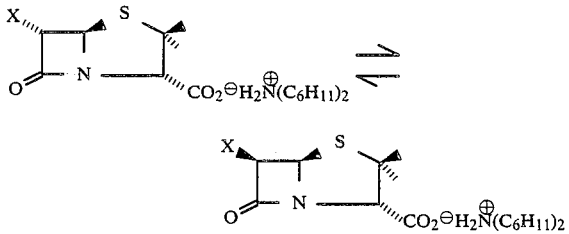

General Procedure

A suspension of the corresponding dicyclohexylammonium 6α-halopenicillanate (10 mmol; X=Cl: 4.17 g, X=Br: 4.61 g, X=I: 5.08 g) and sodium carbonate (1.06 g; 10 mmol) or potassium carbonate (1.38 g; 10 mmol) in a 1:1 (v/v) mixture of dimethylsulphoxide (or dimethylformamide) and water (10 ml) was stirred at room temperature (20°–25° C.) or at slightly elevated temperature (35°–40° C.) for 72 to 120 hours. Ethyl acetate (20 ml) and water (10 ml) were added, the apparent pH of the mixture was adjusted to 1.8 with 4N hydrochloric acid, and the crystalline dicyclohexylammonium chloride thus formed was filtered off and washed with ethyl acetate (5 ml). From the filtrate, the organic layer was separated and the aqueous phase extracted with ethyl acetate (15 ml). The combined organic extracts were washed with water (2×5 ml), dried (MgSO$_4$), and concentrated to about 25 ml. Then, the apparent pH of the resulting solution was adjusted to 7.5 with dicyclohexylamine to give precipitation of a crystalline product. The mixture was kept in a refrigerator overnight, and the crystals were collected by filtration, washed with ethyl acetate (5 ml), diethyl ether, and dried to give a 1st crop of crystalline material. Concentration of the

EXAMPLE 2

Dicyclohexylammonium 6β-halopenicillanates

Reaction

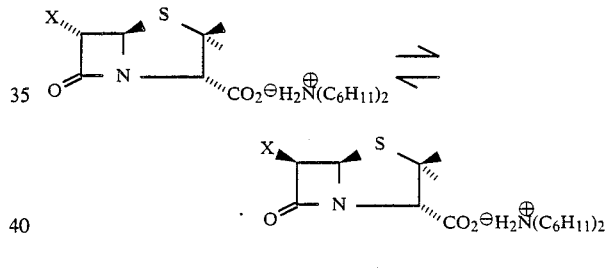

General Procedure

To a suspension of the dicyclohexylammonium 6β-halopenicillanate (50 mmol; X=Cl: 20.85 g, X=Br: 23.07 g, X=I: 25.42 g) in a 1:1 (v/v) mixture of dimethyl sulphoxide (or dimethylformamide) and water (50 ml) was added 50 mmol of base (potassium carbonate, sodium carbonate, trisodium phosphate or triethylamine). The mixture was stirred at room temperature (20°–25° C.) or at elevated temperature (35°–60° C.) for a period of between 20 and 120 hours. Ethyl acetate (100 ml) and water (50 ml) were added, and the apparent pH of the mixture was adjusted to 1.7 with 4N sulphuric acid. The organic phase was separated and the aqueous phase reextracted with ethyl acetate (20 ml). The combined organic extracts were washed twice with water (10 ml), dried (MgSO$_4$) and adjusted to an apparent pH of 7.5 by addition of dicyclohexylamine with stirring. The crystalline precipitate thus formed was cooled in ice-water (2 hours), filtered off, washed with cold ethyl acetate and ether, and dried to afford a 1st crop of substantially pure 6β-halopenicillanate. Concentration of of the mother liquor to about 20–25 ml furnished a 2nd crop of crystalline material containing mainly the 6β-epimer.

The yield of crystalline dicyclohexylammonium 6-halopenicillanate recovered in the 1st crop and the α:β ratio of the product are shown in Table 2 for a series of products prepared according to the described procedure.

TABLE 2

| Ex. No. | X | Solvent Mixture Ratio | Base | Reaction Temp. (°C.) | Time (h) | Yield (%) | Ratio α:β | Crystalline material recovered as 1st crop Yield β % |
|---|---|---|---|---|---|---|---|---|
| 2a | Br | DMSO—H$_2$O 1:1 | K$_2$CO$_3$ | 25 | 26 | 45 | 4:96 | 43.2 |
| 2b | Br | DMSO—H$_2$O 1:1 | K$_2$CO$_3$ | 25 | 98 | 52 | 1:99 | 51.5 |
| 2c | Br | DMSO—H$_2$O 1:1 | Na$_2$CO$_3$ | 25 | 48 | 51 | 1:99 | 50.5 |
| 2d | Br | DMSO—H$_2$O 1:1 | Na$_2$CO$_3$ | 25 | 71 | 61 | 1:99 | 60.4 |
| 2e | Br | DMSO—H$_2$O 1:1 | (C$_2$H$_5$)$_3$N | 25 | 120 | 34 | 4:96 | 32.6 |
| 2f | Br | DMSO—H$_2$O 1:1 | Na$_2$CO$_3$ | 35 | 41 | 59 | 2:98 | 57.8 |
| 2g | Br | DMSO—H$_2$O 1:1 | Na$_2$CO$_3$ | 35 | 96 | 61 | 1:99 | 60.4 |
| 2h | I | DMSO—H$_2$O 1:1 | Na$_2$CO$_3$ | 35 | 96 | 65 | 2:98 | 63.7 |
| 2i | Br | DMSO—H$_2$O 1:1 | K$_2$CO$_3$ | 50 | 48 | 55 | 2:98 | 53.9 |
| 2j | Br | DMSO—H$_2$O 1:1 | Na$_2$PO$_4$ | 50 | 23 | 45 | 2:98 | 44.1 |
| 2k | Br | DMSO—H$_2$O 1:1 | Na$_2$CO$_3$ | 60 | 22 | 59 | 2:98 | 57.2 |
| 2l | Cl | DMF—H$_2$O 1:1 | K$_2$CO$_3$ | 27 | 96 | 22 | 1:99 | 21.8 |
| 2m | Br | DMF—H$_2$O 1:1 | K$_2$CO$_3$ | 27 | 96 | 49 | 1:99 | 48.5 |
| 2n | Br | DMF—H$_2$O 1:1 | K$_2$CO$_3$ | 50 | 20 | 40 | 1:99 | 39.6 |

EXAMPLE 3

Dicyclohexylammonium 6β-bromopenicillanate

Reaction

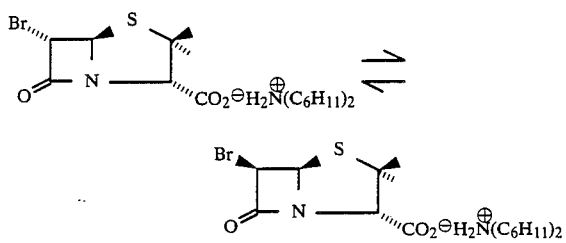

General Procedure

A stirred suspension of dicyclohexylammonium 6α-bromo-penicillanate (230.7 g; 0.5 mol) and sodium carbonate (53.0 g; 0.5 mol) in a mixture of dimethyl sulphoxide (250 ml) and water (250 ml) was treated at room temperature or at slightly elevated temperature (35°–40° C.) for a period of 68 to 120 hours. Then, ethyl acetate (1.5 liter) and water (500 ml) were added, and the apparent pH of the mixture was adjusted to 1.3 with 4N sulphuric acid. The organic phase was separated, clarified by filtration, and washed with water (2×500 ml). The apparent pH of the resulting organic solution was adjusted to 7.5 by addition of dicyclohexylamine with stirring. The crystalline material which precipitated was collected by filtration, washed with ethyl acetate (250 ml) and acetone (500 ml) to yield a 1st crop of substantially pure 6β-bromo compound. A 2nd crop of crystalline material, containing the corresponding 6α-epimer as the major compound, was obtained on concentration of the mother liquor.

Table 3 shows the results of a number of epimerization reactions performed according to the described method.

TABLE 3

| Example No. | Reaction Temp. (°C.) | Time (h) | 1st crop % | 1st crop α:β | 2nd crop % | 2nd crop α:β | Total % α | Total % β |
|---|---|---|---|---|---|---|---|---|
| 3a | 25 | 68 | 48 | 5:95 | 33 | 90:10 | 32.1 | 48.9 |
| 3b | 35 | 96 | 60 | 1:99 | 16 | 85:15 | 14.2 | 61.8 |
| 3c | 35 | 120 | 63 | 1:99 | 19 | 90:10 | 17.7 | 64.3 |
| 3d | 35 | 120 | 64 | 1:99 | 21 | 80:20 | 17.4 | 67.6 |
| 3e | 40 | 96 | 70.5 | 1:99 | 9 | 60:40 | 6.1 | 73.4 |
| 3f | 40 | 120 | 64.4 | 1:99 | 3.6 | 50:50 | 2.4 | 65.6 |

EXAMPLE 4

Dicyclohexylammonium 6β-bromopenicillanate

A suspension containing 230.7 g (0.5 mol) of dicyclohexylammonium 6α-bromopenicillanate and 0.5 mol of a base (sodium carbonate, potassium carbonate or triethylamine) in 500 ml of a 1:1 (v/v) mixture of dimethylformamide (or dimethyl sulphoxide) and water was stirred vigorously at conditions as indicated in Table 4 below). Then, the general procedure of Example 3 was followed to provide the title compound as summarized in Table 4 below.

TABLE 4

| Ex. No. | Solvent Mixture | Ratio | Base | Reaction Temp. (°C.) | Time (h) | Yield (%) | Ratio α:β | Crystalline material recovered as 1st crop Yield β (%) |
|---|---|---|---|---|---|---|---|---|
| 4a | DMF—H$_2$O | 1:1 | Na$_2$CO$_3$ | 25 | 72 | 47 | 4:96 | 45.1 |
| 4b | DMF—H$_2$O | 1:1 | K$_2$CO$_3$ | 25 | 72 | 48 | 2:98 | 47.0 |
| 4c | DMSO—H$_2$O | 1:1 | (C$_2$H$_5$)$_3$N | 35 | 144 | 44 | 2:98 | 43.1 |

EXAMPLE 5

Dicyclohexylammonium 6β-bromopenicillanate

Treatment of a vigorously stirred suspension of dicyclohexylammonium 6α-bromopenicillanate (9.23 kg, 20 mol) and sodium carbonate (2.12 kg, 20 mol) in a mixture of dimethyl sulphoxide (10 liter) and water (10 liter) at 45° C. for 96 hours, followed by a work-up procedure according to that described in Example 3, afforded a first crop of 5.35 kg (58%) of the title compound containing about 1% of the corresponding 6β-epimer. Concentration of the mother liquor yielded a second crop of 1.20 kg (13%) of crystalline material showing a 20:80 ratio between the 6β- and 6α-bromo epimers.

EXAMPLE 6

6β-Bromopenicillanic acid

A suspension of dicyclohexylammonium 6α-bromopenicillanate (4.61 g, 10 mmol) and sodium carbonate (1.06 g, 10 mmol) in a 1:1 (v/v) mixture of dimethyl sulphoxide and water (10 ml) was stirred vigorously at 40° C. for 96 hours. After cooling to 0° C., the slightly yellowish precipitate was filtered off, washed with icecold solvent mixture (2×1 ml), dried, and suspended in ether (30 ml) and water (10 ml). The apparent pH of the stirred mixture was adjusted to 1.6 with 4N sulphuric acid, the aqueous layer was separated and re-extracted with ether (10 ml), and the combined organic phases were washed with water (2×2 ml), dried (MgSO$_4$), treated with decolourizing carbon 0.15 g; stirring for 30 minutes), and filtered. To the filtrate was added hexane (10 ml), the mixture was concentrated to about 10–12 ml, and the white crystals thus precipitated were filtered off, washed with hexane-ether (9:1),and dried to give 1.59 g (56.8%) of pure 6β-bromopenicillanic acid; $[\alpha]_D^{20}+258.8°$ (c 0.5, CHCl$_3$).

EXAMPLE 7

Potassium 6β-bromopenicillanate

A stirred mixture of dicyclohexylammonium 6β-bromopenicillanate (46.15 g, 100 mmol; as prepared in Example 3d) and potassium acetate (10.80 g; 110 mmol) was dissolved at 35°–40° C. in an n-butanol saturated with water (500 ml). The resulting solution was filtered and the filtrate concentrated at reduced pressure to azeotropically remove the water. The crystalline product which precipitated was filtered off, washed with n-butanol (3×20 ml) followed by acetone (3×20 ml), and dried to yield 29.85 g (93.8%) of pure potassium 6β-bromopenicillanate; $[\alpha]_D^{20}+255.9°$ (c 0.5; 1M phosphate buffer pH 7).

Anal. Found: C: 30.24, H: 2.87, Br: 25.12, N: 4.35, S: 9.97%. Calculated for C$_8$H$_9$BrNO$_3$SK: C: 30.19, H: 2.85, Br: 25.11, N: 4.40, S: 10.08%.

EXAMPLE 8

Sodium 6β-bromopenicillanate

Dicyclohexylammonium 6β-bromopenicillanate (46.15 g, 100 ml; as prepared in Example 3d) was suspended in ethyl acetate (500 ml), water (250 ml) was added, and the pH of the stirred mixture was adjusted to 1.7 with 4N sulphuric acid. The organic layer was separated, washed with water (50 ml), and dried (MgSO$_4$). Addition to the stirred filtrate of 1M methanolic so acetate (100 ml) during 40 minutes precipitated the desired compound as white needles. After stirring for a further hour, the crystals were collected by filtration, washed with ethyl acetate (2×20 ml), and dried to afford 25.10 g (83.1%) of pure sodium 6β-bromopenicillanate.

Anal. Found: C. 31.85, H: 3.04, Br: 26.53, N: 4.56, S: 10.60%. Calculated for C$_8$H$_9$BrNO$_3$SNa: C: 31.80, H: 3.00, Br: 26.45, N: 4.64, S: 10.61%.

Concentration of the mother liquor provided an additional 3.25 g (10.8%) of the desired salt.

EXAMPLE 9

Pivampicillin 6β-bromopenicillanate

Dicyclohexylammonium 6β-bromopenicillanate (50 g, 108.34 mmol; as prepared in Example 3c, 1st crop) was slurried in ethyl acetate-saturated water (540 ml), and seeding crystals of pivampicillin 6β-bromopenicillanate (1 g) were added. To the stirred suspension was added during 75 minutes a solution of pivampicillin hydrochloride (65 g; 130 mmol) in ethyl acetate-saturated water (540 ml). The mixture was stirred for a further 2 hours, the crystals were filtered off, washed with ethyl acetate-saturated water (300 ml) followed by hexane (2×250 ml), and dried to afford 78.4 g (95.0%) of the desired compound as white needles; $[\alpha]_D°+223.2°$ (c 0.5 EtOH).

Anal. Found: C. 47.42, H: 5.40, Br: 10.58, N: 7.36, S: 8.54, H$_2$O 2.51%. Calculated for C$_{30}$H$_{39}$BrN$_4$O$_9$S$_2$, H$_2$O: C: 47.31, H: 5.43, Br: 10.49, N: 7.36, S: 8.42, H$_2$O: 2.37%.

EXAMPLE 10

Bacampicillin 6β-bromopenicillanate

To a stirred suspension of dicyclohexylammonium 6β-bromopenicillanate (46.15 g, 100 mmol; as prepared in Example 3c, 1st crop) in water (800 ml) was added dropwise during 75 minutes a solution of bacampicillin hydrochloride (60.24 g, 120 mmol) in water (800 ml). After stirring for an additional 2 hours, the crystals were filtered off, washed with water (2×150 ml) followed by hexane (2×250 ml), and dried to yield 66.3 g (85.8%) of the desired compound.

Anal. Found: C: 45.24, H: 5.21, Br: 10.50, N: 7.27, S: 8.30, H$_2$O: 3.53%. Calculated for C$_{29}$H$_{37}$BrN$_4$O$_{10}$S$_2$, 1.5 H$_2$O: C: 45.08, H: 5.22, Br: 34, N: 7.25, S: 8.30, H$_2$O: 3.49%.

EXAMPLE 11

Pivampicillin 6β-iodopenicillanate

Treatment of a suspension of dicyclohexylammonium 6β-iodopenicillanate (2.54 g, 5 mmol; as prepared in Example 2h) in ethyl acetate-saturated water (50 ml) with a solution of pivampicillin hydrochloride (3.0 g, 6 mmol) in ethyl acetate-saturated water (50 ml) in a similar way as described in Example 9 yielded 3.64 g (90.0%) of the title compound as white needles.

Anal. Found: C: 44.72, H: 5.11, I: 15.64, N: 6.95, S: 7.96, H$_2$O: 2.25%. Calculated for C$_{30}$H$_{29}$IN$_4$O$_9$S, H$_2$O: C: 44.56, H: 5.11, I: 15.69, N: 6.93, S: 7.93, H$_2$O: 2.23%.

EXAMPLE 12

Bacampicillin 6β-iodopenicillanate

In a similar way as described in Example 10 for the corresponding 6β-bromo-derivative, dropwise addition of a solution of bacampicillin hydrochloride (4.82 g, 9.6 mmol) in water (80 ml) to a stirred suspension of dicyclohexylammonium 6β-iodopenicillanate (4.07 g, 8.0 mmol; as prepared in Example 2h) in water (80 ml) afforded 5.52 g (84.2%) of the title compound as white crystals.

Anal. Found: C: 42.54, H: 4.93, I: 15.42, N: 6.81, S: 7.86, H$_2$O: 3.18%. Calculated for C$_{29}$H$_{37}$N$_4$O$_{10}$S$_2$, 1.5 H$_2$O: C: 42.49, H: 4.92, I: 15.48, N: 6.84, S: 7.82, H$_2$O: 3.30%.

EXAMPLE 13

Pivampicillin-6β-bromopenicillanate

A. Dicyclohexylammonium 6β-bromopenicillanate

A stirred suspension of dicyclohexylammomiun 6α-bromopenicillanate (92.2 g, 0.2 mol) and sodium carbonate (21.2 g, 0.2 mol) in a mixture of dimethyl sulphoxide (100 ml) and water (100 ml) was agitated at 60° C. for 24 hours.

Then the mixture was cooled to 5° C., filtered and washed with water (200 ml).

The product was reslurried in water (500 ml, the pH adjusted to 6.0 with $H_3PO_4$ (85%), filtered off, washed with water (200 ml) and dried to yield 45 g (48.8%) of substantially pure dicyclohexylammonium 6β-bromopenicillanate which was directly used in the following step.

B. Pivampicillin 6β-bromopenicillanate

The above dicyclohexylammonium 6β-bromopenicillanate (45 g, 97.5 mmol) was slurried in ethyl acetate-saturated water (500 ml), and seeding crystals of pivampicillin 6β-bromopenicillanate (1 g) were added. To the stirred suspension was added from a dropping funnel during 75 minutes a solution of pivampicillin hydrochloride (58.5 g, 117 mmol) in ethyl acetate-saturated water (500 ml). The mixture was stirred for a further 2 hours, the crystals were filtered off, washed with ethyl acetate-saturated water (300 ml) followed by hexane (2×250 ml), and dried to afford 70.6 g (95.0%) of the desired compound as white needles; $[\alpha]_D^{20} + 223.2°$ (c 0.5, EtOH).

Anal. Found: C: 47.37, H: 5.41, Br: 10.56, N: 7.37, S: 8.52, $H_2O$: 2.55%. Calculated for $C_{30}H_{39}BrN_4O_9S_2$, $H_2O$: C: 47.31, H: 5.43, Br: 10.49, N: 7.36, S: 8.42, $H_2O$: 2.37%.

EXAMPLE 14

Potassium 6β-bromopenicillanate

Dicyclohexylammonium 6β-bromopenicillanate (3.32 kg, 5.0 moles) was dissolved in a mixture of methylene chloride (6 l) and methanol (3 l). The solution was filtered and potassium 6β-bromopenicillanate was precipitated by adding a filtered solution of potassium 2-ethylhexanoate (5.5 mol) in isopropanol (16 l) during 2½ hours. The agitation was continued for another hour, the product was filtered off, washed with isopropanol (4 l) and hexane (4 l).

Air-drying over night afforded 90-93% of substantially pure potassium 6β-bromopenicillanate with analysis in agreement with Example 7.

What we claim is:

1. A method for the preparation of a compound of the formula I

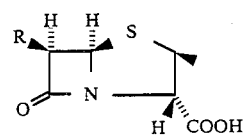

in which R stands for chlorine, bromine or iodine, and salts thereof, which comprises epimerizing a dicyclohexylammonium salt of a 6α-halopenicillanic acid suspended in a mixture of water and an aprotic organic solvent and in the presence of a base which catalyzes the epimerization to precipitate the less soluble dicyclohexylammonium salt of the corresponding 6β-halopenicillanic acid thus formed, which can be recovered as such or directly be converted to the corresponding acid or to another salt.

2. A method according to claim 1, in which R stands for bromine.

3. A method according to claim 1, in which R stands for iodine.

4. A method according to claim 1, in which the organic solvent is a polar organic solvent selected from the group consisting of dimethyl sulphoxide, dimethylformamide, dimethylacetamide, diethylformamide, hexamethylphosphoramide and tetrahydrothiophene 1,1-dioxide.

5. A method according to claim 4, in which the epimerization is performed at a temperature in the range from 20° C. to 80° C. for a period of 12 to 180 hours.

6. A method according to claim 5, in which the ratio between the organic solvent and water in the solvent mixture is from 4:1 and 1:4.

7. A method according to claim 1, in which the precipitated salt is converted to another salt by a double decomposition.

8. A method according to claim 1, in which the 6β-halopenicillanic acid is liberated and subsequently converted to a salt.

9. A method according to claim 7, in which the other salt is a salt with a β-lactam antibiotic containing a free amino group.

10. A method according to claim 8, in which the liberated 6β-halopenicillanic acid is converted to a salt with a β-lactam antibiotic containing a free amino group.

11. A method according to claim 7, in which the claimed salt is a salt with 6β-bromopenicillanic acid.

12. A method according to claim 9, in which the β-lactam antibiotic is pivampicillin.

13. A method according to claim 9, in which the β-lactam antibiotic is bacampicillin.

14. A process according to claim 1 for obtaining a high yield of substantially pure 6β-halopenicillanic acid which comprises preparing a suspension of a dicyclohexylammonium salt of a 6α-halopenicillanic acid in a mixture of water and an aprotic organic solvent and a base and stirring said suspension at 20° to 80° C. for 12-180 hours to precipitate the resulting dicyclohexylammonium salt of the corresponding 6β-halopenicillanic acid thus formed.

15. A process according to the claim 14 wherein the suspension temperature is stirred at a temperature of 30° to 60° C. and the ratio of organic solvent to water is between 2:1 and 1:2.

16. A process according to claim 15 wherein the base is an alkali metal carbonate and the organic solvent is dimethylsulphoxide or dimethylformamide.

* * * * *

UNITED STATES PATENT AND TRADEMARK OFFICE
CERTIFICATE OF CORRECTION

PATENT NO. : 4,847,266

DATED : July 11, 1989

INVENTOR(S) : HANSEN ET AL

It is certified that error appears in the above-identified patent and that said Letters Patent is hereby corrected as shown below:

Title page, first inventor's name should read:

Erik T. Hansen, Fredensborg;

Col. 7, line 3, change "6β-" to -- 6α- --.

Col. 7, line 37, change "n" to -- $\underline{n}$ --.

Col. 7, line 59, change "so" to -- sodium --.

Signed and Sealed this

Twenty-ninth Day of May, 1990

Attest:

HARRY F. MANBECK, JR.

Attesting Officer — Commissioner of Patents and Trademarks